United States Patent
Tronnes et al.

(10) Patent No.: US 8,061,026 B2
(45) Date of Patent: Nov. 22, 2011

(54) METHOD FOR MAKING SMOOTH TRANSITIONS BETWEEN DIFFERING LEAD SEGMENTS

(75) Inventors: Carole A. Tronnes, Stillwater, MN (US); Daniel J. Stetson, Lino Lakes, MN (US); Brian T. Stolz, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/707,116

(22) Filed: Feb. 17, 2010

(65) Prior Publication Data

US 2010/0212154 A1     Aug. 26, 2010

Related U.S. Application Data

(60) Provisional application No. 61/154,461, filed on Feb. 23, 2009.

(51) Int. Cl.
*H01R 43/00* (2006.01)
(52) U.S. Cl. .............. 29/857; 29/825; 29/858; 156/258; 156/304.2; 604/523
(58) Field of Classification Search ............. 29/825, 29/857, 858; 156/258, 304.2; 604/523
See application file for complete search history.

(56) References Cited

U.S. PATENT DOCUMENTS

| | | | |
|---|---|---|---|
| 5,234,416 A * | 8/1993 | Macaulay et al. ............ 604/527 |
| 5,240,537 A * | 8/1993 | Bodicky ............... 156/244.13 |
| 5,241,957 A | 9/1993 | Camps | |
| 5,255,704 A * | 10/1993 | Bennett ............... 137/454.5 |
| 5,354,326 A | 10/1994 | Comben et al. | |
| 5,473,812 A * | 12/1995 | Morris et al. ............. 29/825 |
| 5,545,149 A * | 8/1996 | Brin et al. ............. 604/265 |
| 5,811,043 A * | 9/1998 | Horrigan et al. ........... 264/138 |
| 6,157,862 A | 12/2000 | Brownlee et al. | |
| 6,216,045 B1 | 4/2001 | Black et al. | |
| 6,245,053 B1 * | 6/2001 | Benjamin ............ 604/523 |
| 6,374,476 B1 * | 4/2002 | Ponzi et al. ........... 29/527.1 |
| 6,489,562 B1 | 12/2002 | Hess et al. | |
| 6,852,261 B2 * | 2/2005 | Benjamin ............ 264/248 |
| 7,184,838 B2 | 2/2007 | Cross, Jr. | |
| 7,302,299 B2 | 11/2007 | Wojciechowicz | |
| 2001/0016702 A1 * | 8/2001 | Benjamin ............ 604/19 |
| 2006/0271136 A1 | 11/2006 | Wojciechowicz | |
| 2007/0025784 A1 * | 2/2007 | Ito et al. ............ 399/329 |
| 2007/0225784 A1 | 9/2007 | Bly et al. | |

* cited by examiner

*Primary Examiner* — Carl Arbes

(57) ABSTRACT

A method for forming a lead body includes contacting a proximal section of the lead body having a lumen and a first lead body characteristic to a distal section of the lead body having a lumen and a second lead body characteristic. The proximal and distal sections are contacted such that their lumens are axially aligned. A lap band is disposed about a portion of the proximal section and a portion of the distal section, and is thermally formed to the proximal and distal sections. Axially compressive pressure is applied to the lap band as the lead body is being thermally formed. The pressure applied is sufficient to result in the lead body having an outer diameter in regions proximally and distally adjacent to the lap band that are substantially the same to an outer diameter in a region formed by the lap band.

22 Claims, 8 Drawing Sheets

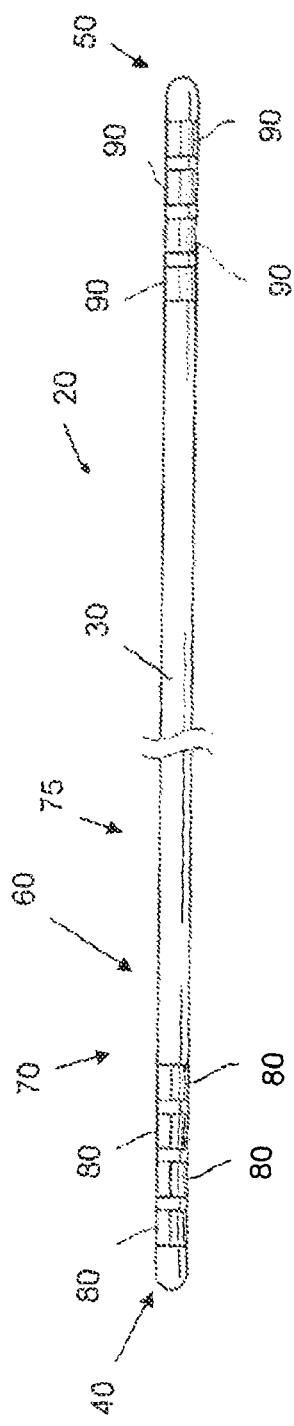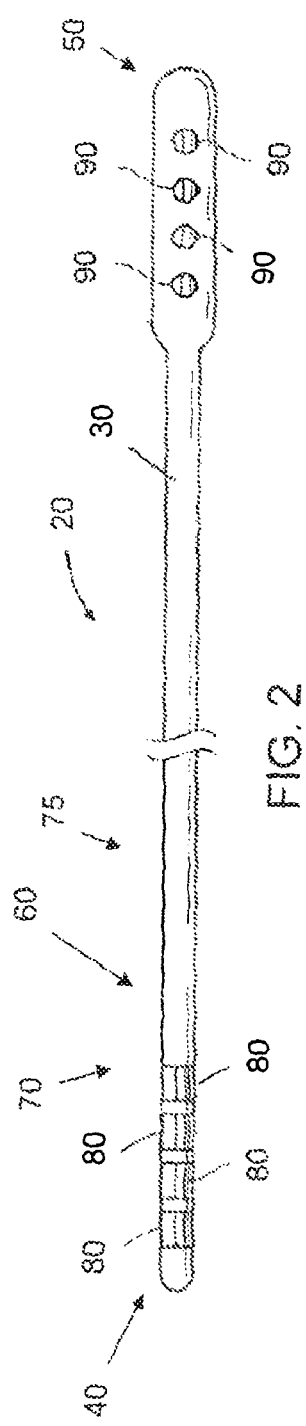

A)
500
B)
360
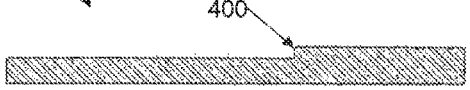
400
C)
360  400  320
FIG. 9

A)  ← 510
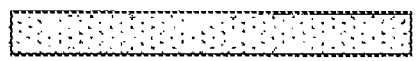
B)  ← 350
320
FIG. 10

METHOD FOR MAKING SMOOTH TRANSITIONS BETWEEN DIFFERING LEAD SEGMENTS

RELATED APPLICATION

This application claims the benefit of priority to U.S. Provisional Patent Application No. 61/154,461, filed on Feb. 23, 2009, which application is hereby incorporated herein by reference in its entirety to the extent that it does not conflict with the disclosure presented herein.

FIELD

This application relates to medical devices, more particularly implantable medical leads and to methods for manufacturing leads.

BACKGROUND

Electrical stimulation technology is expanding in scope, resulting in therapies that place leads in more and more areas of the body and in leads that have increasing levels of complexity. The stiffness of a lead body can be important for its function in many ways. For example, a very flexible lead body may be desirable for implantation in tissues that experience a lot of movement. A stiffer lead body may be important for guiding through tissue or for insertion into a device, such as an electrical signal generator. For example, if the portion of a lead to be inserted into a device is not sufficiently stiff, pushing the lead into a receptacle of the device may be difficult.

In transitioning from a stiff to a more flexible segment along the length of a lead, it is desirable for the transition to be smooth to spread any stresses out evenly over the length of the transition. Many ways of transitioning between segments of differing lead flexibilities have been devised. However, some are impractical from a manufacturing perspective or result in undesired characteristics. For example, lap bonding of two sections of differing stiffnesses can result in a reliable bond that spreads stresses out over the length of the lap bonded section; however, such lap bonding also results in increased thickness of the lead body. Such leads have a bulge in their outer diameter, which may be undesirable.

BRIEF SUMMARY

Leads having smooth transitions between differing segments and having uniform outer diameters along and in proximity to the transition section are described herein. Practical methods for manufacturing such leads are also described herein.

In various embodiments, a method for forming a lead body having a transition from a section having a first lead body characteristic to a section having a second lead body characteristic, as described herein, includes contacting a proximal section of the lead body having the first lead body characteristic to a distal section of the lead body having the second lead body characteristic. The proximal and distal sections of the lead body define lumens. The proximal and distal sections are contacted such that the lumen of the proximal section is axially aligned with the lumen of the distal section. The method further comprises disposing a lap band about a portion of the proximal section and a portion of the distal section, and thermally forming the lead body by bonding the lap band to the proximal and distal sections. Axially compressive pressure is applied to the lap band as the lead body is being thermally formed. The pressure applied is sufficient to result in the lead body having an outer diameter in regions proximally and distally adjacent to the lap band that are substantially the same as an outer diameter in a region formed by the lap band.

In various embodiments, a method for forming a lead body having a transition from a section having a first lead body characteristic to a section having a second lead body characteristic, as described herein, includes contacting a proximal section of the lead body to a distal section of the lead body. The distal section of the lead body defines a lumen extending through the distal section, has a substantially uniform inner diameter, has a first outer diameter along a first length from a proximal end of the first precursor to a first location distal the proximal end, and has a second outer diameter distal the first location. The first outer diameter is smaller than the second outer diameter. The proximal section of the lead body defines a lumen extending through the proximal section, has a substantially uniform inner diameter, has a first outer diameter along a first length from a distal end of the second precursor to a first location proximal the distal end to form the proximal section of the lead body, and has a second outer diameter proximal the location proximal the distal end. The first outer diameter is smaller than the second outer diameter. The proximal and distal sections are contacted such that the lumen of the proximal section is axially aligned with the lumen of the distal section. A lap band is disposed about a portion of the proximal section and a portion of the distal section and is thermally bonded to the proximal and distal sections.

BRIEF DESCRIPTION OF THE DRAWINGS

FIGS. 1-2 are schematic drawings of side views of representative leads.

FIGS. 9A-C are schematic drawings illustrating a method for making a distal section of a lead as shown in FIG. 8A.

FIGS. 10A-B are schematic drawings illustrating a method for making a proximal section of a lead as shown in FIG. 8A.

Figure 3:
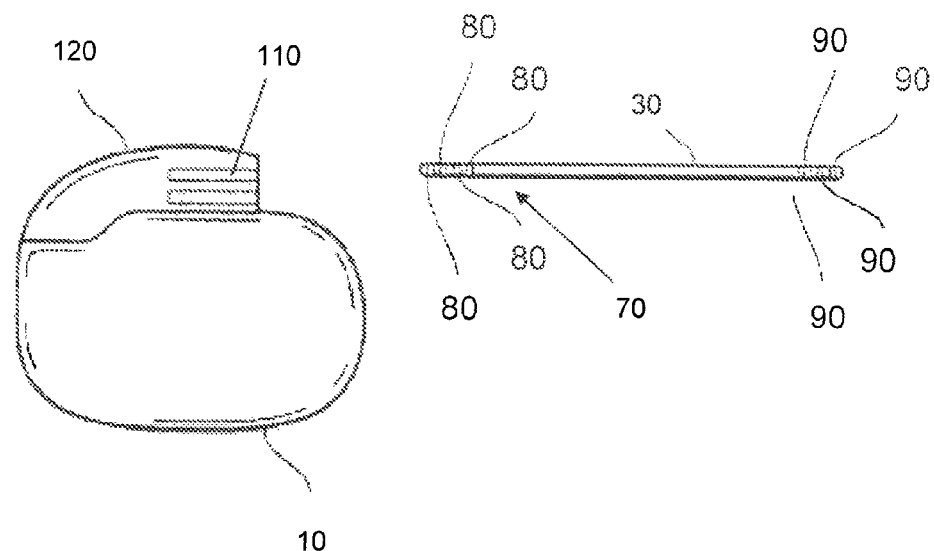
FIG. 3 is a schematic drawing of a side view of a representative system including an electrical signal generator and a lead.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used herein "substantially" means to a great extent or degree. Thus, two items or characteristics that are substantially the same are the same to a great extent or degree. For example, the two items or characteristics may be the same to the extent that processes for producing the things or characteristics are reproducible. Alternatively, or in addition, two things or characteristics that are substantially the same may be generally indistinguishable when considered for their intended purpose or purposes. For example, if two sections of a lead are to have substantially the same outer diameter so that the lead may be slidably disposed in an introducer with tight tolerances, then if the both sections slide through the introducer without difficulty the two outer diameters can be considered substantially the same.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to medical leads, such as leads and lead extensions, having smooth transitions between segments having differing characteristics. The leads have uniform diameters along and in proximity to the transition section.

Leads as described herein may be used in conjunction with any suitable electrical medical device, such as an electrical signal generator system or a monitoring system. Examples of electrical signal generator systems that such leads may be used with include spinal cord stimulators, gastric stimulators, sacral nerve stimulators, deep brain stimulators, cochlear implants, defibrillators, pacemakers, and the like. In many embodiments, such electrical medical devices are implantable.

Any suitable type of lead may be adapted according to the teaching presented herein. By way of example and with reference to FIG. 1 and FIG. 2, examples of representative leads 20 are shown. Leads 20, as shown in FIGS. 1 and 2, contain four exposed electrical contacts 80 and four electrodes 90. However, leads 20 may contain any suitable number of electrodes 90 or contacts 80. The contacts 80 are disposed in proximity to the proximal end 40 of the lead 20. The electrodes 90 are disposed in proximity to the distal end 50 of the lead 20. Conductive wires (not shown) electrically couple discrete contacts 80 with discrete electrodes 90. The conductors run within the lead body 30. The contacts 80 are configured to couple electrical contacts of an electrical signal generator, such that signals generated by the active device may be applied to a tissue of a patient in which the distal end 50 of the lead 20 is implanted. A signal generated by the device is transmitted via a contact 80 along a conductor to an electrode 90 and to tissue in which the electrode 90 is implanted. The lead 20 shown in FIG. 1 is of a type generally referred to as a percutaneous lead. The lead 20 shown in FIG. 2 is a paddle-type, or surgical, lead. However, it will be understood that any lead configuration may be employed in accordance with the teachings provided herein.

Still with reference to FIGS. 1-2, at some point along the length of the lead body 30 there is a transition region 60 where the lead body 30 transitions from a section 70 having a first characteristic to a section having a second characteristic 75. The transition may be between any two characteristics. For example the transition may be between a region having more rigidity to a region having more flexibility, between a region having one color and a region having another color, or the like. The transition region 60 may be located at any suitable position along the length of the lead body 30.

In various embodiments, the lead body transitions at a transition region 60 from a first rigid section 70 to a second more flexible section 75. The rigid section 75 includes the proximal end 40 of the lead body 30 and is sufficiently stiff to allow easy and reliable insertion into a receptacle of an active electrical medical device. For example, in some embodiments, the rigid section 75 has a flexural modulus of about 0.003 lbf-in$^2$ or greater.

For example and with reference to FIG. 3, the rigid proximal section 70 of the depicted lead body 30 is configured to be inserted into a receptacle 110 of a header 120 of an implantable electrical signal generator 10. The receptacle 110 includes internal electrical contacts (not shown) configured to contact an electrically couple with contacts 80 of the lead. Hermetically sealed feedthroughs (not shown) electrically couple the internal contacts to electronics in the primary hermetically sealed housing of the signal generator 10. The proximal portion 70 of the lead body 30 is sufficiently rigid to allow for reproducible and ready insertion into, or withdrawal from, the receptacle 110 to provide reliable electrical coupling between contacts 80 of the lead and the receptacle 110 of the active electrical device 10. While not shown, it will be understood that leads configured to be coupled to lead extensions or other devices having receptacles configured to receive the lead may also benefit from having a rigid proximal section.

Figure 4A:
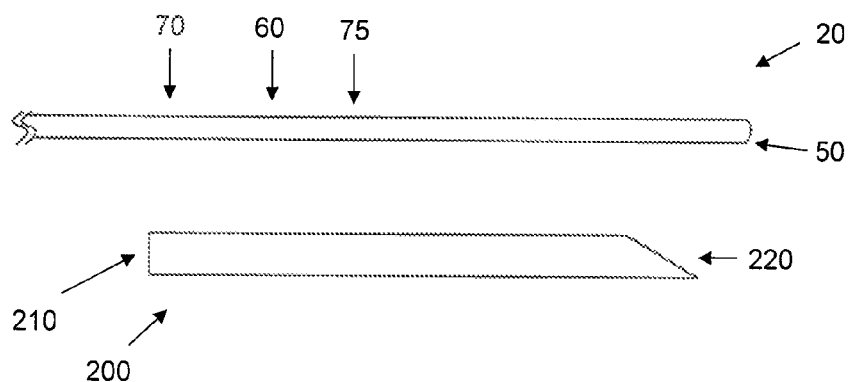
FIGS. 4A-B are schematic drawings of side views (4A, exploded) of a representative lead and introducer.
Figure 4B:
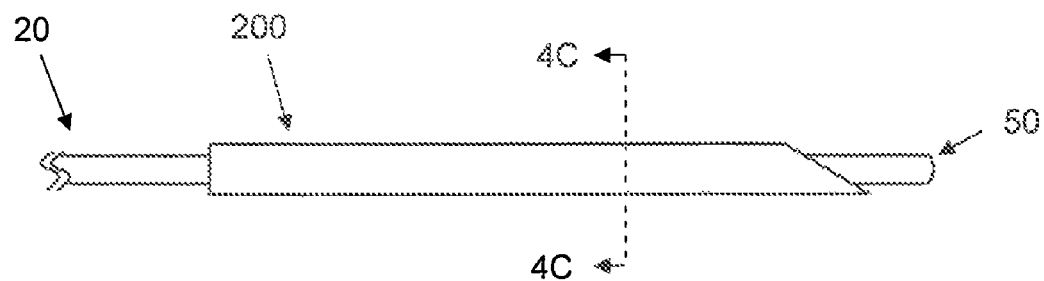
Figure 4C:
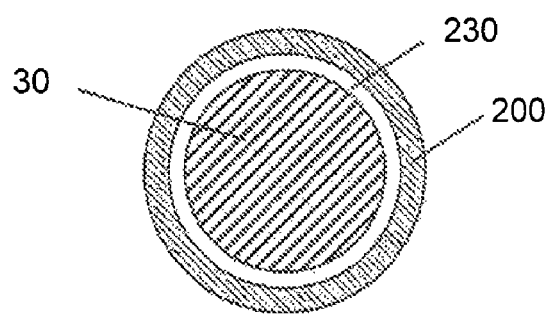
FIG. 4C is a schematic drawing of a cross section through the lead and introducer shown in FIG. 4B taken through line 4C-4C.

In the embodiments depicted in FIGS. 1-3, the transition section 60 through which the lead body 30 transitions from a section 70 having a first characteristic, e.g. rigidity, to a section 75 having a second characteristic, e.g. flexibility, has a substantially uniform outer diameter in the transition section 60 and proximal and distal to the transition section 60. In addition to aesthetic purposes, the substantially uniform outer diameter may serve a variety of functional purposes. For example and with reference to FIGS. 4A-C, a lead 20 having a substantially uniform outer diameter may be beneficial when the lead 30 is introduced into a patient through an introducer 200, such as a Touhy needle. The depicted introducer 200 has a proximal end 210, a distal end 220 and a lumen 230 extending through the introducer 200 from the proximal end 210 to the distal end 220. The lumen 230 is configured to slidably receive the lead 20. The clearance between the outer diameter of the lead body 30 and the inner diameter of the introducer 200 is desirably kept small so that use of excessively small gauge introducer needles, which may cause trauma to the patient, is avoided. Due to the typically small clearance between the lead body 30 and the inner surface of the introducer 200 defining the lumen 230, it is desirable to minimize differences in the outer diameter in the transition region 60 and those regions proximal and distal to the transition region 60 so that lead 20 may be readily inserted into, or withdrawn from, the introducer 200.

Leads that have a smooth transition between a section having a first characteristic and a section having a second characteristic and which have a substantially uniform diameter throughout the transition section and proximal and distal to the transition section are described below. Methods for making such leads are also described in more detail below. Referring now to FIGS. 5-9, various representative longitudinal sections of lead bodies and methods are shown. For the purposes of clarity only polymeric tubes or portions thereof that are used to form the lead body are shown. It will be understood that leads may include other components such as a shield, conductive wires, contacts, electrodes, reinforcement members such as a mesh, and the like. In the embodiments depicted, a proximal section 310 of the lead body is shown as being the section having the first characteristic 70 and a distal section of the lead body 320 is shown as being the section having the second characteristic 75. Of course, it will be understood that the distal section may have the first characteristic and the proximal section may have the second characteristic.

Figure 5:
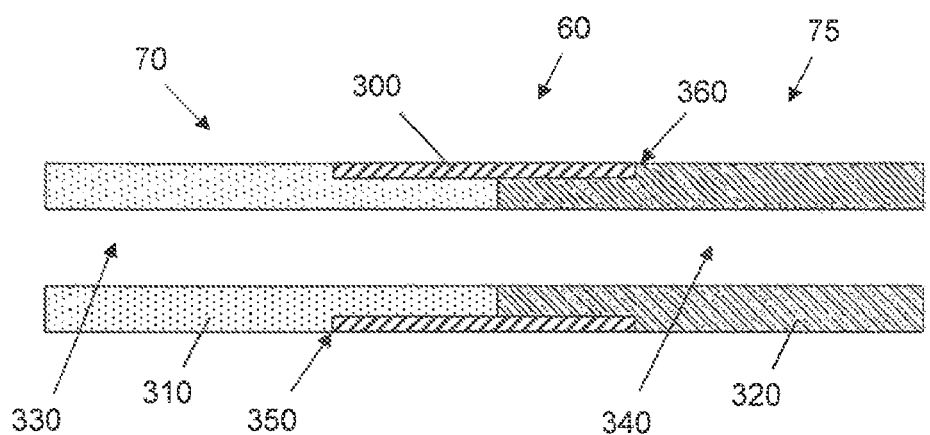
FIG. 5 is a schematic drawing of a representative lead illustrating a method for making the lead.

In the embodiment depicted in FIG. 5, the proximal section 310 of the lead body is contacted with the distal section 320 of the lead body and the lumen 330 of the proximal section 310 is axially aligned with the lumen 340 of the distal section 320. The distal end of the proximal section 310 is in contact with the proximal end of the distal section 320. The inner diameters of the distal and proximal sections of the lead body are substantially the same. The proximal lead body section 310 has a first outer diameter from the distal end to a location 350 proximal the distal end and has a second outer diameter proximal to the location 350. The second outer diameter is greater than the first outer diameter. The distal lead body section 320 has a first outer diameter from the proximal end to a location 360 distal the proximal end and has a second outer diameter distal to the location 360. The second outer diameter is greater than the first outer diameter. The first outer diameter of the proximal section 310 is substantially the same as the first outer diameter of the distal section 320. A lap band 300 has a thickness that is about half the difference between the second outer diameter and the first outer diameter of either the proximal 310 or distal 320 sections. The lap band 300 has a length that is substantially the same as the cumulative length of: the distance from the distal end of the proximal section 310 to the location 350 proximal the distal end; and the distance from the proximal end of the distal section 320 to the location 360 distal the proximal end. Thus, the lap band 300 is configured to abut the shoulder formed at the location 350 where the proximal section 310 transitions from the first outer diameter to the second outer diameter and is configured to abut the shoulder at the location 360 where the distal section 320 transitions from the first outer diameter to the second outer diameter, when the distal end of the proximal section 310 and the proximal end of the distal section 320 are in contact. The area of the lead body formed by the lap band 300 is the transition section 60 of the lead body, and the outer diameter of the lead body is substantially uniform along the transition region 60 and proximal and distal to the transition section 60.

The lead body may be formed by thermally bonding the lap band 300 to the proximal section 310 and the distal section 320. In various embodiments, such lap bonding occurs when the lap band material is heated to 100° C. or higher depending on the material. The lap band 300, proximal section 310 and distal section 320 may be made of any suitable thermoplastic polymer. Examples of suitable thermoplastic polymers include polyurethane, polysulfone, polyethylene, and polypropylene. In various embodiments, the lap band 300, proximal section 310, and the distal section 320 are made of the same type of polymeric material. In the case of polyurethane, lap bonding may occur at about 250° C. to about 300° C.

When each of the lap band 300, the proximal section 310, and the distal section 320 are made of the same type of polymeric material and the proximal section is more rigid than the distal section, similar materials of different durometers may be used.

Referring now to FIGS. 6A-B, a proximal section 310 of a precursor to a lead body is contacted with a distal section 320 of a lead body such that the lumen 330 of the proximal section 310 is axially aligned with the lumen 330 of the distal section 320. The distal end of the proximal section 310 is in contact with the proximal end of the distal section 320. A lap band 300 is disposed about the proximal 310 and distal 320 sections. The lead body (see FIG. 6B) is thermally formed by bonding the lap band 300 to the proximal 310 and distal 320 sections. An axially compressive force is applied to the lap band 300 as the lead body is being thermally formed. Sufficient axial pressure is applied to result in the lead body having an outer diameter in regions proximal and distal the transition section 60 formed by the lap band that are substantially the same as the outer diameter in the region 60 formed by the lap band 300.

To prevent collapse of the lumen 370 as the lead body is being formed and to provide sufficient normal force to the axially compressive force applied to the lap band 300 to form the uniform transition section 60, the proximal 310 and distal 320 sections may be placed about a mandrel (not shown) having an outer diameter substantially the same as the inner diameter of the sections 310, 320. To achieve sufficient axially compressive force to result in a substantially uniform outer diameter of the lead body in the transition section 60, a die (not shown) may be used to provide the axial pressure. It will be understood that the amount of axial pressure applied necessary to achieve a substantially uniform outer diameter will vary from material to material and process conditions to process conditions. For purposes of example, when employing distal 320 and proximal 310 polyurethane sections having an 0.050 inch OD×0.030 inch ID and durometers of 55 D and 75 D and a polyurethane lap band 300 having a 55 D durometer and an 0.057 inch OD×0.051 inch ID, axial pressure pneumatically applied by a die for a time of 5 seconds, when the transition region 60 was heated at 250° C., was sufficient to result in a substantially uniform outer diameter when formed about a mandrel.

Referring now to FIGS. 7A-B, an alternative lead and method are shown. In the depicted embodiment, the proximal section 310 having the first characteristic has substantially uniform outer and inner diameters. The distal section 320 having the second characteristic has a substantially inner diameter forming a lumen 340 and has first and second outer diameters. The first outer diameter being smaller than the second outer diameter. The region of the distal portion 320 having the first outer diameter extends from the proximal end to a location 360 distal the proximal end. The second outer diameter extends distally from the location 360. The inner diameter of the proximal section 310 is substantially the same as the first outer diameter of the distal section 320. The outer diameter of the proximal section 310 is substantially the same as the outer diameter of the distal section 320. The proximal section 310 is disposed about the section of the distal section 320 that has the first outer diameter. The distal end of the proximal section 310 is in contact with the proximal face of the shoulder formed at the location 360 as the distal section 320 transitions from the first outer diameter to the second outer diameter. In the depicted embodiments, the proximal section 310 and the distal section 320 are co-axial or axially aligned. A lap bad 300 is disposed about the proximal 310 and distal 320 sections at the region where the sections 310, 320 intersect. As discussed above with regard to FIG. 6, the lead body is thermally formed while axially compressive force is applied to the lap band to result in a lead body having a substantially uniform outer diameter in the transition section 60 defined by the length of the lap band 300 and proximal and distal to the transition section 60 (see FIG. 7B).

Figure 6:
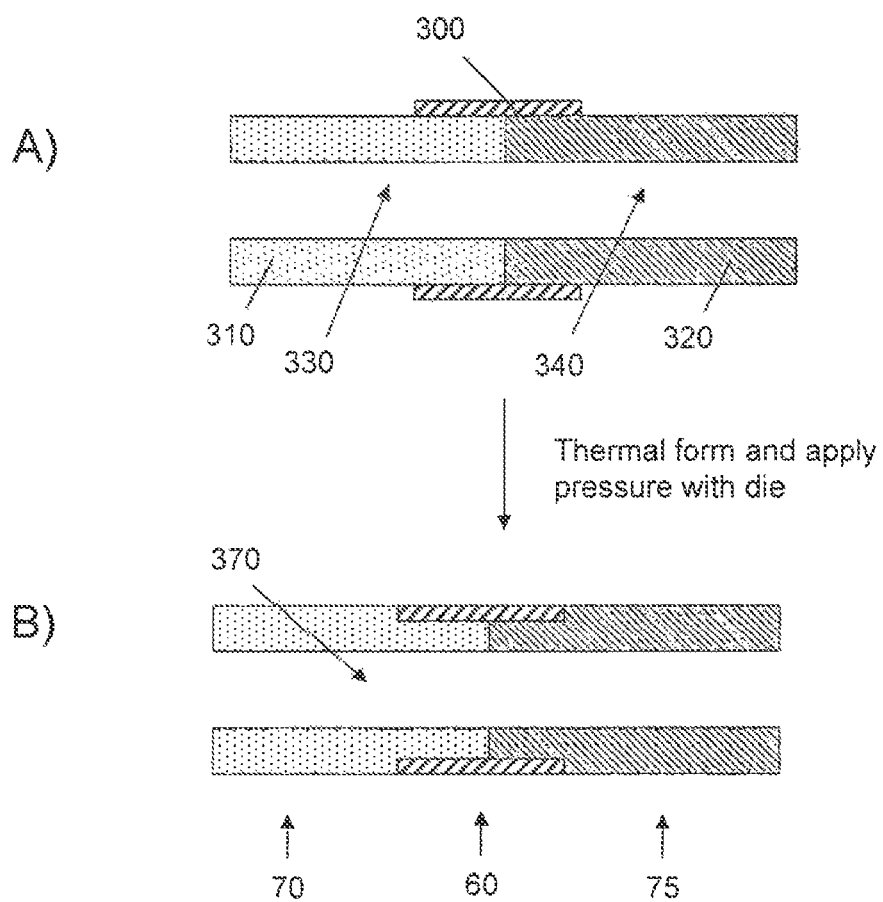
FIGS. 6A-B are schematic drawings of a representative lead illustrating a method for making the lead.
Figure 7:
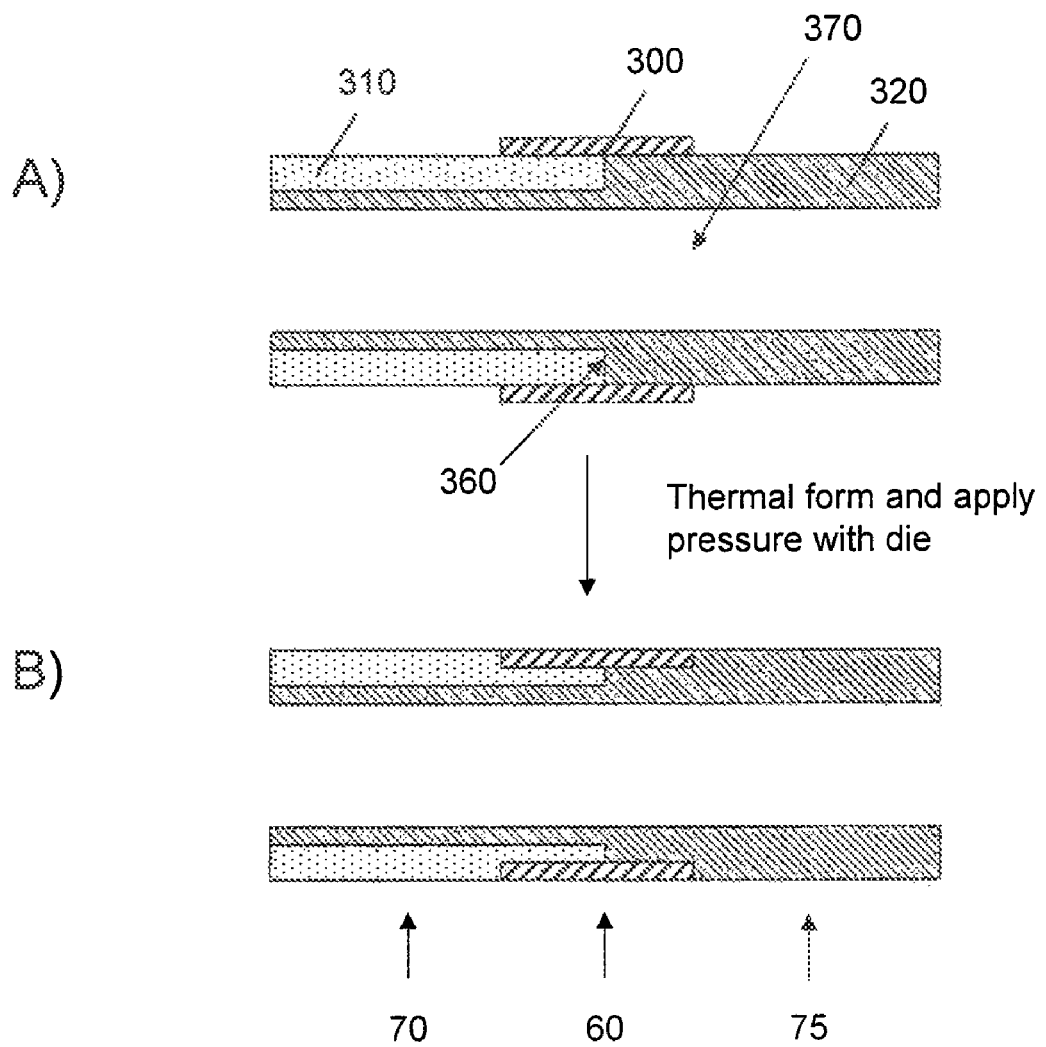
FIGS. 7A-B are schematic drawings of a representative lead illustrating a method for making the lead.

In the embodiment depicted in FIG. 7, the portion of the distal section 320 having the first outer diameter is co-extensive with proximal section 310. Such an arrangement may be advantageous relative to the arrangement depicted in FIG. 6 because the surface area of the bond between the two sections 310, 320 is increased. However, the processing steps or manufacturing costs associated with a distal section 320 having two outer diameters as shown in FIG. 7A may be increased relative to a distal section 320 as shown in FIG. 6.

Figure 8:
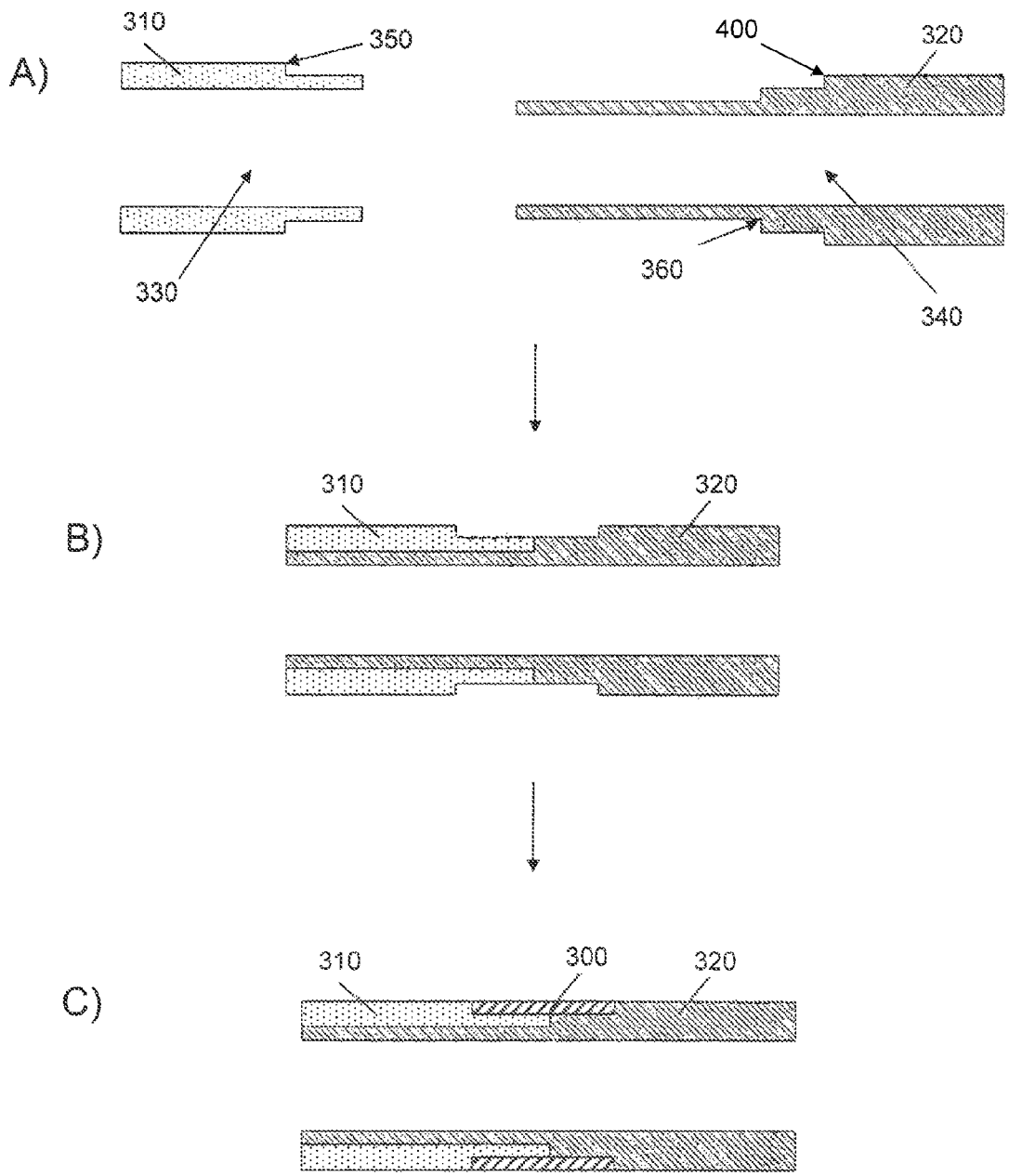
FIGS. 8A-C are schematic drawings of a representative lead illustrating a method for making the lead.

Referring now to FIG. 8, an alternative embodiment of a lead body and a process are shown. In the depicted embodiment, a proximal section 310 having a first characteristic and a distal section 320 having a second characteristic are shown. The proximal section 310 has a substantially uniform inner diameter forming a lumen 330, and has first and second outer diameters. The first outer diameter is smaller than the second outer diameter. A region of the proximal section 310 extending from the distal end to a location 350 proximal the distal end has the first outer diameter. A region of the proximal section 310 extending proximally from the location 350 has the second outer diameter.

The distal section 320 depicted in FIG. 8 has a substantially uniform inner diameter forming a lumen 340, and has first, second and third outer diameters. The first outer diameter is smaller than the second outer diameter. The second outer diameter is smaller than the third outer diameter. A region of the distal section 320 extending from the proximal end to a first location 360 distal the proximal end has the first outer diameter. A region of the distal section 320 extending distally from the first location 360 to a second location 400 distal the first location 360 has the second outer diameter. A region of the distal section 320 extending distally from the second location 400 has the third outer diameter.

The inner diameter of the proximal section 310 is substantially the same as the first outer diameter of the distal section 320. The first outer diameter of the proximal section 310 is substantially the same as the second outer diameter of the distal section 320. The second outer diameter of the proximal section 310 is substantially the same as the third outer diameter of the distal section 320.

In the embodiment depicted in FIGS. 8A-C, the proximal section 310 is placed about the portion of the distal section 320 having the first outer diameter such that the distal end of the proximal section 310 contacts the shoulder formed at the transition from the first outer diameter to the second outer diameter of the distal section 320 (see FIG. 8B). A lap band 300 is placed about the portion of the proximal section 310 having the first outer diameter and the portion of the distal section 320 having the second outer diameter such that the lap band 300 contacts the shoulder of the proximal section 320 formed at the transition from the first outer diameter to the second outer diameter and contacts the shoulder of the distal section 320 formed at the transition from the second outer diameter to the third outer diameter (see FIG. 8C). The lead body may then be thermally formed to produce a lead body having a substantially uniform outer diameter along the transition section formed by the lap band 300 and proximal and distal to the transition region (see FIG. 8C).

Proximal and distal sections as described above that have differing outer diameters along their length may be made by any suitable process such as machining, molding or etching. With reference to FIGS. 9-10, process schemes for forming the proximal section 310 (FIG. 10) or distal section 320 (FIG. 9) depicted in FIG. 8 are shown for purposes of example. In FIG. 9, illustrated is a precursor polymeric tube 500 having a substantially uniform outer diameter, which corresponds to the third outer diameter of the distal section 320 (depicted in FIG. 8), and a substantially uniform inner diameter (see FIG. 9A). As depicted, a portion of the polymeric precursor 500 may be removed; e.g., by etching or machining, or a series of steps made via a stretching and thermal forming. In the embodiment depicted in FIG. 9B, the portion of the thickness from the proximal end to the first location 360 or the second location 400 may be removed to form intermediates. In the case of removal to the first location 360, a sufficient amount of the precursor is removed to leave a section having an outer diameter equivalent to the first outer diameter of the proximal section 320. In the case of removal to the second location 400, a sufficient amount of the precursor is removed to leave a section having an outer diameter equivalent to the second outer diameter of the proximal section 320. The intermediates may be further processed; e.g. via etching or machining, to arrive at the completed distal section 320 (see FIG. 9C).

With reference to FIGS. 10A-B, a precursor 510 is processed such that a portion of the thickness of the precursor 510 is removed from the distal end to a first location 350 proximal the distal end to result in the proximal section 310.

Of course any other suitable method for making proximal and distal sections as described herein may be employed.

Thus, embodiments of the METHOD FOR MAKING SMOOTH TRANSITIONS BETWEEN DIFFERING LEAD SEGMENTS are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for forming a lead body having a transition from a section having a first lead body characteristic to a section having a second lead body characteristic wherein the first and second lead body characteristics are selected from durometer, rigidity, flexibility, color, and combinations thereof, the method comprising:

contacting (i) a proximal section of the lead body having the first lead body characteristic to (ii) a distal section of the lead body having the second lead body characteristic, wherein the proximal section of the lead body defines a lumen, wherein the distal section of the lead body defines a lumen, and wherein the proximal section is contacted with the distal section such that the lumen of the proximal section is axially aligned with the lumen of the distal section;

disposing a lap band about a portion of the proximal section and a portion of the distal section;

thermally forming the lead body by bonding the lap band to the proximal and distal sections; and applying axially compressive pressure to the lap band as the lead body is being thermally formed, wherein the pressure applied is sufficient to result in the lead body having an outer diameter in regions proximally and distally adjacent to the lap band that are substantially the same to an outer diameter in a region formed by the lap band.

2. The method of claim 1, wherein contacting the proximal section to the distal section such that the lumen of the proximal section is axially aligned with the lumen of the distal section comprises disposing the proximal section and the distal section about a mandrel, wherein the mandrel axially aligns the lumens of the proximal and distal sections.

3. The method of claim 2, wherein the mandrel has an outer diameter dimension substantially the same as the inner diameter dimension of the lumens of the proximal and distal sections.

4. The method of claim 1, wherein the distal section of the lead body has a substantially uniform inner diameter, and has a first outer diameter along a length from a proximal end to a location distal the proximal end, and has a second outer diameter distal the location of the distal portion of the proximal end, wherein the first outer diameter is smaller than the second outer diameter.

5. The method of claim 4, wherein contacting the proximal section to the distal section such that the lumen of the proximal section is axially aligned with the lumen of the distal section comprises disposing at least a distal portion of the proximal section about at least a portion of the distal section having the first outer diameter.

6. The method of claim 4, wherein the proximal section of the lead body has a thickness and wherein half the difference in the second outer diameter and the first outer diameter of the distal section of the lead body is substantially the same as the thickness of the proximal section.

7. The method of claim 1, wherein the proximal section of the lead body has a substantially uniform inner diameter, has a first outer diameter along a length from a distal end to the location proximal the distal end, and has a second outer diameter proximal the location of the proximal portion of the distal end wherein the first outer diameter is smaller than the second outer diameter.

8. The method of claim 7, wherein contacting the proximal section to the distal section such that the lumen of the proximal section is axially aligned with the lumen of the distal section comprises disposing at least a proximal portion of the distal section about at least a portion of the proximal section having the first outer diameter.

9. The method of claim 8, wherein the distal section of the lead body has a thickness and wherein the thickness of the distal section is about half the difference of the second outer diameter and the first outer diameter of the proximal section.

10. The method of claim 1, wherein the first lead body characteristic is a relative stiffness and the second lead body characteristic is a relative flexibleness.

11. A method for forming a lead body having a transition from a first lead body characteristic to a section having a second lead body characteristic, wherein the first and second lead body characteristics are selected from durometer, rigidity, flexibility, color, and combinations thereof, the method comprising:
   providing a distal section of the lead body having a substantially uniform inner diameter, a first outer diameter along a first length from a proximal end to a first location distal the proximal end, and a second outer diameter distal the first length, wherein the first outer diameter is smaller than the second outer diameter,
   wherein a lumen extends through the proximal section of the lead body from the proximal end of the section to a distal end;
   providing a proximal section of the lead body having a substantially uniform inner diameter, a first outer diameter along a first length from a distal end to a first location proximal the distal end, and a second outer diameter proximal the location proximal the distal end, wherein the first outer diameter is smaller than the second outer diameter,
   wherein a lumen extends through the distal section of the lead body from the distal end of the section to a proximal end;
   contacting the proximal section to the distal section such that the lumen of the proximal section is axially aligned with the lumen of the distal section;
   disposing a lap band about a portion of the proximal section and a portion of the distal section;
   bonding the lap band to the proximal and distal sections.

12. The method of claim 11, wherein contacting the proximal section to the distal section comprises contacting the distal end of the proximal section to the proximal end of the distal section.

13. The method of claim 12, wherein the lap band has a thickness, wherein the first outer diameter of the proximal section is substantially the same as the first outer diameter of the distal section,
   wherein the second outer diameter of the proximal section is substantially the same as the second outer diameter of the distal section,
   wherein the thickness of the lap band is about half the difference of the second outer diameter of the proximal section and the first outer diameter of the proximal section, and
   wherein forming the lead body comprises forming a lead body having a substantially uniform outer diameter from a location proximal the lap band region to a location distal the lap band region.

14. The method of claim 11, wherein the distal section of the lead includes a second length from the first location to a second location distal the first location, wherein the outer diameter of the second length is the second outer diameter of the distal section and wherein the distal section has a third outer diameter distal the second location, wherein the third outer diameter is greater than the second outer diameter.

15. The method of claim 14, wherein contacting the proximal section to distal section comprises disposing at least a distal portion of the proximal section about at least a portion of the first length of the distal section.

16. The method of claim 15, wherein the inner diameter of the proximal section is substantially the same as the outer diameter of the first section of the distal section, wherein the first outer diameter of the proximal section is substantially the same as the second outer diameter of the distal section, wherein the second outer diameter of the proximal section is substantially the same as the third outer diameter of the distal section, wherein the lap band has a thickness that is about half the difference between the second outer diameter of the proximal section and the first outer diameter of the proximal section, and
   wherein disposing the lap band about a portion of the proximal section and a portion of the distal section comprises disposing the lap band about the first length of the proximal section and the second length of the distal section.

17. The method according to claim 1, wherein the first characteristic is rigidity and the second characteristic is flexibility.

18. The method according to claim 1, wherein the first characteristic and the second characteristic are durometers and the first characteristic and the second characteristic are substantially different.

19. The method according to claim 1, wherein the first characteristic is a first color and the second characteristic is a second color.

20. The method according to claim 11, wherein the first characteristic is rigidity and the second characteristic is flexibility.

21. The method according to claim 11, wherein the first characteristic and the second characteristic are durometers and the first characteristic and the second characteristic are substantially different.

22. The method according to claim 11, wherein the first characteristic is a first color and the second characteristic is a second color.

* * * * *